(12) United States Patent
Van Der Loo

(10) Patent No.: US 8,095,208 B2
(45) Date of Patent: Jan. 10, 2012

(54) SYSTEM FOR DETERMINATION OF AN EFFECTIVE TRAINING HEART RATE ZONE AND USE OF SUCH A SYSTEM

(75) Inventor: Johannes Van Der Loo, Boskoop (NL)

(73) Assignee: Nederlandse Organisatie Voor Toegepast-Natuurwetenschappelijk Onderzoek TNO, Delft (NL)

(*) Notice: Subject to any disclaimer, the term of this patent is extended or adjusted under 35 U.S.C. 154(b) by 131 days.

(21) Appl. No.: 12/307,449

(22) PCT Filed: Jul. 5, 2007

(86) PCT No.: PCT/NL2007/050330
§ 371 (c)(1),
(2), (4) Date: Apr. 3, 2009

(87) PCT Pub. No.: WO2008/004870
PCT Pub. Date: Jan. 10, 2008

(65) Prior Publication Data
US 2009/0253992 A1 Oct. 8, 2009

(30) Foreign Application Priority Data
Jul. 5, 2006 (EP) ..................................... 06076357

(51) Int. Cl.
*A61B 5/0402* (2006.01)
(52) U.S. Cl. .......................... 600/520; 600/509; 600/549
(58) Field of Classification Search .................. None
See application file for complete search history.

(56) References Cited

U.S. PATENT DOCUMENTS

| | | | |
|---|---|---|---|
| 4,312,358 A | 1/1982 | Barney | |
| 4,450,843 A | 5/1984 | Barney et al. | |
| 5,125,412 A | 6/1992 | Thornton | |
| 5,394,879 A | 3/1995 | Gorman | |
| 6,149,602 A | 11/2000 | Arcelus | |
| 2001/0023320 A1* | 9/2001 | Kinnunen et al. | 600/500 |
| 2001/0027266 A1* | 10/2001 | Hautala et al. | 600/16 |

(Continued)

FOREIGN PATENT DOCUMENTS

EP 0255621 A1 2/1988

(Continued)

OTHER PUBLICATIONS

Burton, A.C. (1934). The application of the theory of heat flow to the study of energy metabolism. Journal of Nutrition. 7, 497-453.*

(Continued)

*Primary Examiner* — Carl H Layno
*Assistant Examiner* — Paula J Stice
(74) *Attorney, Agent, or Firm* — Leydig Voit & Mayer Ltd.

(57) ABSTRACT

System for effective training heart rate zone determination, the system comprising:—a training module adapted to determine target training heart rate zone based on at least one stored parameter;—at least one sensor for measuring core temperature of a user's body during training;—at least one sensor for measuring a user's heart rate during training;—a compensation module, which is arranged for compensating the target training heart rate zone based on said core temperature;—an indicating module adapted to compare the users heart rate to an effective training heart rate zone based on information from the compensation module and to inform the user when the heart rate exceeds or drops under the effective training heart rate zone. The invention further relates to use of such a system.

18 Claims, 1 Drawing Sheet

U.S. PATENT DOCUMENTS

| 2002/0155924 | A1 | 10/2002 | Dardik |
| 2003/0004403 | A1 | 1/2003 | Drinan et al. |
| 2004/0039254 | A1* | 2/2004 | Stivoric et al. ............ 600/300 |

FOREIGN PATENT DOCUMENTS

| EP | 1512370 A1 | 3/2005 |
| GB | 2378762 A | 2/2003 |
| GB | 2408105 A | 5/2005 |
| WO | WO 96/20640 | 7/1996 |

OTHER PUBLICATIONS

Wooden, K.M and Walsberg G.E. (2002). Effect of environmental temperature on body temperature and metabolic heat production in a heterothermic rodent, *Spermophilus tereticaudus*. The Journal of Experimental Biolgy 205, 2099-2105.*

International Search Report PCT/NL2007/050330 dated Oct. 22, 2007.

* cited by examiner

SYSTEM FOR DETERMINATION OF AN EFFECTIVE TRAINING HEART RATE ZONE AND USE OF SUCH A SYSTEM

FIELD OF THE INVENTION

The invention relates to a system for determination of an effective training heart rate zone.

BACKGROUND

Such systems are known in the prior art. For instance, U.S. Pat. No. 6,104,947 relates to a method for determining exertion levels in fitness or athletic training and for determining the stress caused by the training by means of heartbeat rate measurement. Determining of the heartbeat rate is based on an ECG signal. Variations therein are accurately monitored, for example by means of standard deviation. The most important cause of the variation is respiratory arrhythmia. Based on the variations, a corresponding target heartbeat rate range is given or alternatively an alarm is given if a previously set target heartbeat rate range is exceeded or fallen short of Thus, by real-time monitoring of the heartbeat rate variation, the training of the individual person can be optimized.

SUMMARY OF THE INVENTION

However, applicant has found that during training the heartbeat rate is partly used for activity energy and that another part of the heartbeat rate is used to regulate the body temperature. Therefore, the effective training heartbeat rate, which in fact is the activity part of the heartbeat rate can have a different value than the user thinks. Consequently, the effective training heartbeat can be outside the target training heartbeat zone without the user knowing. It is known that exercising is only effective and has physical impact, burning fat or strengthening the body, when the actual heartbeat rate of the user during training does stay in the target heart rate zone. Not knowing the actual effective training heart rate zone can result in hours of training without benefiting thereof.

It is therefore an object of the invention to provide an improved system for determining effective training heart rate zones. More particularly, it is an object of the invention to provide a system for effective training heart rate zone determination that provides effective training levels for the user thereby maximally reducing the risk of over-training or under-training.

The invention provides a system for effective training heart rate zone determination, the system comprising:

a training module adapted to determine target training heart rate zone based on at least one stored parameter;

at least one sensor for measuring core temperature of a user's body during training;

at least one sensor for measuring a user's heart rate during training;

a compensation module, which is arranged for compensating the target training heart rate zone based on said core temperature;

an indicating module adapted to compare the users heart rate to an effective training heart rate zone based on information from the compensation module and to inform the user when the heart rate exceeds or drops under the effective training heart rate zone.

With such a system a user can train at an effective training heart rate zone, thereby taking into account environmental parameters like outside temperature, relative humidity of the air, sun radiation, wind, kind of clothing that the user is wearing and/or activity level of the user. This system is based on the fact that the environmental parameters are reflected in the core temperature of a user. For example, when the outside temperature increases, the core temperature of the user increases as well, be it with a time delay, but the delayed core temperature effect is what really counts for the training load.

According to a further elaboration of the invention, the effective training heart rate zone is composed of the target training heart rate zone and a temperature compensation value. Because of the fact that part of the cardiac output is used for increased perfusion of the skin in order to keep the body of the user at the right temperature, the determined target training heart rate zone has to be changed in order to compensate for the extra beats that are made by the heart serving temperature regulation. The compensation is determined by a temperature compensation value.

In further elaboration of the invention, the compensation module is adapted to use the following function to determine the temperature compensation value:

$$C = P \times (Tc - Tb),$$

wherein C is the temperature compensation value, P is a personal compensation value, Tc is the core temperature and Tb represents an average body temperature.

This means that every degree of temperature difference with respect to the average body temperature, which is approximately 37° C., has an effect on the temperature compensation value. Furthermore, the temperature compensation value is influenced by the personal compensation value, which in fact represents the amount of extra heartbeats per minute a user has to have per degree difference with the average body temperature. The more environmental factors raise the core temperature, the higher the heart rate has to be to effectively train the body.

According to a further aspect of the invention, the compensation module is adapted to store at least the personal compensation value and the average body temperature. The function has to be provided with the personal compensation value and the normal or average body temperature of the person. During training, the compensation module adapts the temperature compensation value constantly according to the change in core temperature. It is possible to store an estimated average body temperature of 37° C., but in fact a user can also determine his own average body temperature by measuring it several times and determine the average of these measurements.

In further elaboration of the invention, the personal compensation value has a value between 0-40, more specific between 10-30. and preferably, the personal compensation value is determined individually per user, for instance with a test. This test can for example be done by performing an exercise with continuous effective power, e.g. on a cycle ergometer, and measuring heart beat and core temperature on a regular basis as they increase. It can also be done by repeating the same exercise in various environmental temperatures after adaptation of the body to that temperature. The personal compensation value can change to certain factors (stress, age, lack of water). Being able to change the personal compensation value is therefore desirable—preferably it would be automatically derived.

According to a further aspect of the invention, the maximum heart rate is determined by a physical test or is based on a known function, like for instance: Maximum Heart Rate=220−Age. Preferably, when being a beginner in the field of training with heart rate monitoring, it is advisable to consult a physician to determine the maximum heart rate. Ideally, a maximum exertion test has to be done to determine the user's physical condition and, wherein the maximum heart rate is measured right after exertion. However, most of the times the maximum heart rate is estimated, for instance with the mentioned commonly known function. This function does not take any other parameter into account than the age of the user, which makes the maximum heart rate not very reliable. Other functions for determining the maximum heart rate are described in Sally Edwards' Heart Rate Monitor Book, Heart Zone Training. For a male person the following functions are known:

220−Age (Non-athletic)
205−Age/2 (fit)
214−(0.8*Age)

For female persons the following functions are known:
226−Age (non-athletic)
211−Age/2 (fit)
209−(0.7*Age)

To determine the maximum heart rate one could also use the following which combines the Miller formula with the research from Londeree and Moeschberger.

Use the Miller formula of MHR=217−(0.85×age) to calculate MHR
    Subtract 3 beats for elite athletes under 30
    Add 2 beats for 50 year old elite athletes
    Add 4 beats for 55+ year old elite athletes
    Use this MHR value for running training
    Subtract 3 beats for rowing training
    Subtract 5 beats for bicycle training In further elaboration of the invention, the target training heart rate zone is based on at least one of the following parameters: maximum heart rate value, resting heart rate value, physical condition, gender, age, weight, training activity. It is common practice to determine the training target heart rate zone on certain percentages of the maximum heart rate value. For instance the lower level of the zone can be determined by taking 65% of the maximum heart rate and the upper level of the zone can be determined by taking 85% of the maximum heart rate. The zone can furthermore be divided into different smaller zones, for example a zone which is effective for burning fat and a zone that is effective when training endurance and lung capacity.

Another way of determining the target training heart rate zone may be with aid of the so-called Karvonen method. This method takes the resting heart rate value into account when determining the minimum and maximum amount of heart rate. Indirectly, the physical condition of the user is taken into account, because when getting in better physical shape, the resting heart rate value drops, which has an influence on the target training heart rate zone. The mentioned percentages and/or lower and upper zone values are not fixed values but can vary according to the source that provides those percentages. These values can also be adapted by taking into account the physical condition of the user, the gender of the user, age and weight of the user and the desired training activity. The latter depends on the kind of activity, for example running, bicycling, swimming etc. and on the desired kind of training, for example fat burning, aerobic training or anaerobic training.

According to a further elaboration of the invention, the system comprises an output device such as a display, sound signal, vibrating signal or other signal that is adapted to display, for example, the effective training heart rate zone and a real-time heart rate. The user of the system can easily monitor whether the heart rate during training stays in the effective training heart rate zone and the user can act or anticipate upon that information by for instance slowing down or accelerating.

According to another aspect of the invention, the indication module is adapted to provide the user with a signal when the heart rate exceeds or drops under the effective training heart rate zone, wherein the signal is at least one of the following: visual signal, audible signal and tactile signal. Such a signal informs the user to accelerate or slow down, even when the user is not watching the display.

Preferably, the indication module is arranged to provide a warning signal when the actual heart rate reaches a dangerous level.

In further elaboration of the invention, the training module, the compensation module and the indication module are part of an electronic device, for instance a watch, an armband, a waistband, a mobile phone, an ergometer, a fitness device, a music device like a MP3-player or the like, wherein the sensors are connectable to, or part of the electronic device. Preferably, the sensors are connectable to the electronic device via a wireless connection. The sensors can also be part of a breast band and be situated around the breast of a user during training or be placed on the sports equipment (such as a fitness device).

The invention further relates to use of a system for effective training heart zone determination to effectively train a user's body. The use of such a system has similar effects and advantages as mentioned with the system for effective training heart rate zone determination.

BRIEF DESCRIPTION OF THE DRAWINGS

The invention will be further elucidated by means of exemplary embodiments with reference to the accompanying drawings in which.

DETAILED DESCRIPTION OF THE INVENTION

Figure 1:
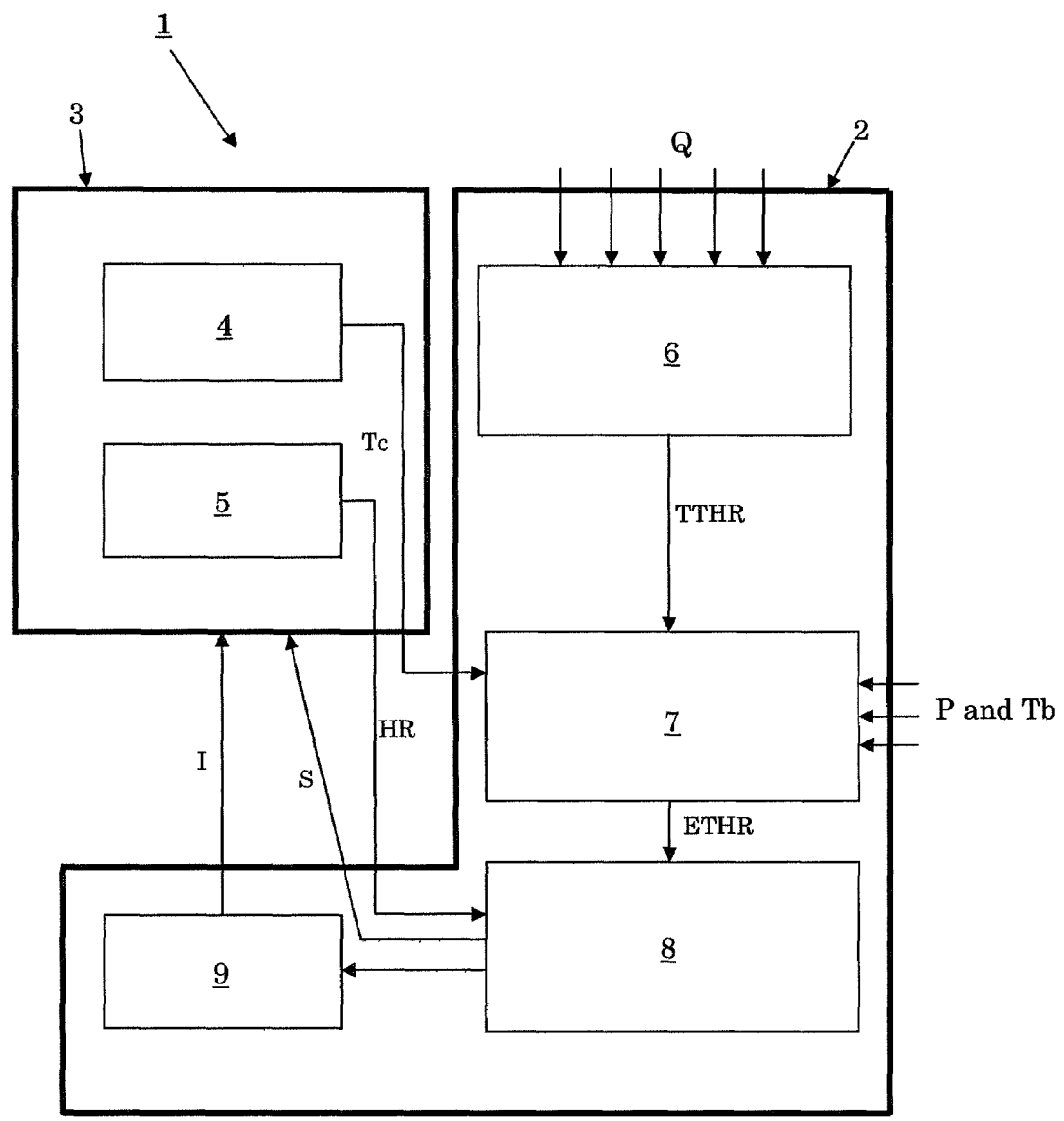
FIG. 1 shows a schematic diagram of a system according to the invention.

The invention will now be described and explained more in detail. In FIG. 1, a system for effective training heart rate zone determination is shown. The system 1 comprises device 2 with a training module 6 adapted to determine a target training heart rate zone TTHR based on at least one stored parameter Q. The device 2 is further provided with at least one sensor 4 for measuring the core temperature Tc of a user's 3 body during training and at least one sensor 5 for measuring a user's 3 heart rate HR during training. The device 2 can for instance be a watch, an armband, a waistband, a mobile phone, a music device like a MP3-player or the like, wherein the sensors 4, 5 are connectable to, or part of the electronic device 2. Preferably, the sensors 4, 5 are connected to the device 2 with a wireless connection.

The device 2 further comprises a compensation module 7 that is able to compensate the target training heart rate zone TTHR with a temperature compensation value C. Also an indicating module 8 is provided that compares the user's heart rate HR to an effective training heart rate zone ETHR based on information from the compensation module 8 and informs the user 3 when the heart rate HR exceeds or drops under the effective training heart rate zone ETHR.

Preferably, the indicating module 8 also warns the user when the heart rate reaches a dangerous level.

At start, a user 3 stores certain parameters in the training module 6 of his electronic device 2. With those parameters the device can determine at least the user's maximum heart rate HRmax. Furthermore, the user 3 connects the temperature sensor 4, which measures his core temperature Tc and the heart rate sensor 5, which monitors the heart rate HR to his body. The training module 6 determines on basis of said HRmax the target training heart rate zone TTHR of the user 3.

For Example:

A user is 40 years old and therefore his estimated HRmax can be 220−40=180 heartbeats per minute. If the user 3 wants to train at a fat burning level, his target training heart rate zone can be for instance between 60% and 70% of his HRmax, being between 108-126 heartbeats per minute.

During training, the sensor 4 constantly sends the actual core temperature Tc of the user 3 to the compensation module 7 of the system 1. The compensation module 7 determines on basis of the core temperature Tc, the effective training heart rate zone ETHR for the user 3.

For Example:

When it is a sunny day the core temperature Tc of the user 3 can be 38.5 degrees. In the compensation module 7 a personal compensation value P and the average body temperature Tb at rest are stored. Assuming that P=20 for this user and the Tb is 37° C., the compensation module 7 determines a temperature compensation value C by using the function: C=P×(Tc−Tb).

Thus C=20×(38.5−37)=30. This means that the user 3 has to reach a heartbeat rate that is 30 beats higher than estimated with the target training heart rate zone TTHR. Consequently, the user 3 has to train with a heart rate being in the effective training heart rate zone ETHR of 138-156 heartbeats per minute to get an effective fat burning training. The indication module 8 provided in the device 2 compares the heart rate HR of the user 3 with the effective training heart rate zone ETHR. If the actual heart rate HR exceeds or drops under the effective training heart rate zone ETHR, the user 3 receives a signal S send by the indication module 8. The user 3 can adapt his training accordingly. Furthermore, the device 2 can be provided with a display 9 that visualizes information I from the indication module 8. The information I enables the user 3 to anticipate by actively keeping his heart rate HR in the effective training heart rate zone ETHR. It is clear that the system 1 continuously updates itself according to differences that occur in core temperature Tc and heart rate HR during the training. In cold weather, the user should sometimes train at a lower HR according to the same formula. E.g. (36.5−37)*20=10 heart beats lower than heart rate zone. This correction helps prevent biomechanical injuries as are often seen as a result of training in cold weather. Consequently, the user 3 trains effectively during the entire training getting the best possible effort out of the training.

Although illustrative embodiments of the present invention have been described in greater detail with reference to the accompanying drawings, it is to be understood that the invention is not limited to these embodiments. Various changes or modifications may be effected by one skilled in the art without departing from the scope or the spirit of the invention as defined in the claims.

The invention claimed is:

1. A system for determining an effective training heart rate zone, the system comprising:
    a training module adapted to determine a target training heart rate (TTHR) zone based on a maximum heart rate of a user, the maximum heart rate being determined based on at least one parameter stored in the training module;
    at least one sensor for measuring a core temperature ($T_c$) of the user during training;
    at least one sensor for measuring a heart rate of the user during training;
    a compensation module, which is arranged for compensating the target training heart rate (TTHR) zone based on an increase in a measurement of the core temperature (Tc), from the at least one sensor for measuring the core temperature, with respect to an average body temperature (Tb) at rest to determine an effective training heart rate (ETHR) zone, wherein the ETHR zone is composed of the TTHR zone having upper and lower range values increased by a temperature compensation value (C) for a current value of the core temperature exceeding the average body temperature, wherein:
    C=P×(Tc−Tb) and wherein P is a personal compensation value representing an amount of extra heartbeats per minute of a user at rest per degree unit temperature difference between the current value of the core temperature and the average body temperature; and
    an indicating module adapted to compare the heart rate of the user to the effective training heart rate zone based on information from the compensation module and to inform the user when the heart rate exceeds or drops under a range specified by the effective training heart rate zone.

2. System according to claim 1, wherein the compensation module is adapted to store at least the personal compensation value and the average body temperature at rest.

3. System according to claim 1, wherein the personal compensation value has a value between 0-40.

4. System according to claim 1, wherein the personal compensation value is determined individually per user.

5. System according to claim 4, wherein the personal compensation value is determined with a test.

6. System according to claim 1, wherein a maximum heart rate is determined by a physical test.

7. System according to claim 1, wherein the target training heart rate zone is based on at least one of the following parameters: maximum heart rate value, resting heart rate value, physical condition, gender, age, weight, and training activity.

8. System according to claim 1, wherein the system comprises a display that is adapted to display the effective training heart rate zone and a real-time heart rate.

9. System according to claim 1, wherein the indication module is adapted to provide the user with a signal when the heart rate exceeds or drops under the effective training heart rate zone.

10. System according to claim 9, wherein the signal is at least one of the following: visual signal, audible signal, and tactile signal.

11. System according to claim 1, wherein the training module, the compensation module and the indication module are part of an electronic device.

12. System according to claim 11, wherein the sensors are connectable to the electronic device via a wireless connection.

13. System according to claim 11, wherein the electronic device is one of the following: a watch, a mobile phone, a music device, or training equipment; and
    wherein the sensors are either connectable to, or part of the electronic device.

14. System according to claim 13 wherein the training equipment is one of the following: a fitness device or a bicycle ergometer.

15. A method of effectively training a user's body wherein the training includes using the system of claim 1 for effective training heart zone determination.

16. System according to claim 1, wherein the personal compensation value has a value between 10-30.

17. System according to claim 1, wherein a maximum heart rate is determined by a known function.

18. System according to claim 17 wherein the known function is:
    Maximum Heart Rate=220−Age (beats per minute).

* * * * *